United States Patent [19]

Igarashi et al.

[11] Patent Number: 5,760,242

[45] Date of Patent: Jun. 2, 1998

[54] METHOD OF PRODUCING A CIS-OXAZOLINE

[75] Inventors: Yoshio Igarashi; Fumihiro Asano; Makoto Shimoyamada; Masayuki Harada; Shigeru Nakano; Ryoji Iwai; Keisuke Yagami; Yuzi Konno, all of Fukushima-ken, Japan

[73] Assignee: Ichikawa Gosei Chemical Co., Ltd., Chibi, Japan

[21] Appl. No.: 762,193

[22] Filed: Dec. 9, 1996

Related U.S. Application Data

[62] Division of Ser. No. 346,746, Nov. 30, 1994, Pat. No. 5,648,534.

[30] Foreign Application Priority Data

Dec. 1, 1993 [JP] Japan .................... 5-301989
Mar. 28, 1994 [JP] Japan .................... 6-57649

[51] Int. Cl.$^6$ .................... C07D 263/52
[52] U.S. Cl. .................... 548/217; 548/224
[58] Field of Search .................... 548/217, 224

[56] References Cited

U.S. PATENT DOCUMENTS

| | | | |
|---|---|---|---|
| 2,518,156 | 8/1950 | Magat | 564/130 |
| 3,523,136 | 8/1970 | Schneider et al. | 564/130 |
| 3,523,137 | 8/1970 | Moore | 564/130 |
| 5,072,024 | 12/1991 | Cesa et al. | 564/130 |
| 5,103,055 | 4/1992 | Cesa | 564/130 |
| 5,187,074 | 2/1993 | Treiber et al. | 435/41 |
| 5,449,830 | 9/1995 | Verhoeven et al. | 564/400 |

FOREIGN PATENT DOCUMENTS

A-0 480 624  2/1991  European Pat. Off. .

OTHER PUBLICATIONS

G. Drefahl et al., "Untersuchungen an cyclischen 1,2-Chloraminen", Journal Für Praktische Chemie, vol. 21, No. 3–4, pp. 204–207 (1963).
STN–Information Service file: REG RN= 79542–17–9 & Laurent, Chem. Abstr. vol. 102:Entry 5254.
G. Drefahl and K. Ponsold, "Addition von Jodisocyanant an unsymmertrische Olefine", Chemische Berichte, vol. 95, pp. 519–523, (1960).
A. Hassner et al., "Addition of Iodine Isocyanate to Olefins. Scope and Synthetic Utility", J. Org. Chem., vol. 32, pp. 540–549 (1967).
W.J. Thompson, "Synthesis and Antiviral Activity of a Series of HIV–1 Protease Inhibitors with Funtionality Tethered to the P1 or P2 Phenyl Substitutes: x–ray Crystal Structure Assisted Design", J. Med. Chem., vol. 35, pp. 1685–1701 (1992).

Merck Index, 10th Edition, Rahway, New Jersey, (1983) p. ONR-77.

Primary Examiner—Donald G. Daus
Attorney, Agent, or Firm—Frommer Lawrence & Haug, LLP

[57] ABSTRACT

1,2-di-substituted indan expressed by general formula (I) wherein X is a substituent which can be drawn out under an acidic condition to form a carbocation at 1-position of an indan skeleton, Y is a halogen atom, and X and Y can be in either cis- or trans-configuration forming either a racemic body or an optically active substance; or 1,2-di-substituted indan expressed by general formula (I') wherein X is a substituent which can be drawn out under an acidic condition to form a carbocation at 1-position of an indan skeleton, and X and OH group can be in either cis- or trans-configuration forming either a racemic body or an optically-active substance; or cis-1,2-epoxyindan expressed by general formula (VI) wherein R is phenyl or a lower alkyl group, oxazoline ring is in cis-configuration forming either a racemic body or an optically active substance is reacted, under an acidic condition, with a nitrile expressed by general formula (II) wherein R is phenyl or a lower alkyl group to produce cis-1-aminoindan-2-ol expressed by general formula (V) wherein $NH_2$ and OH groups are in cis-configuration forming either a racemic body or an optically-active substance.

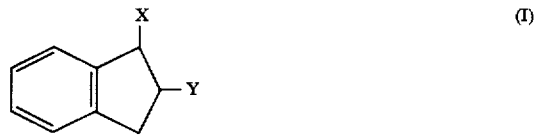

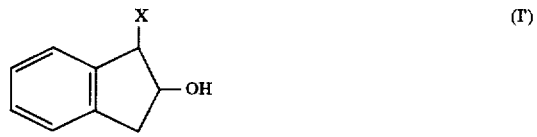

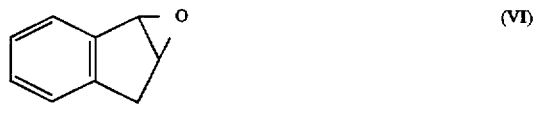

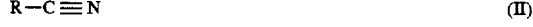

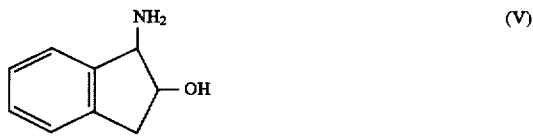

2 Claims, No Drawings

METHOD OF PRODUCING A CIS-OXAZOLINE

This application is a division of application Ser. No. 08/346,746, filed Nov. 30, 1994, U.S. Pat. No. 5,648,534.

BACKGROUND OF INVENTION

1. Field of the Invention

The present invention relates to an industrially useful method of producing cis-1-aminoindan-2-ol.

2. Description of the Prior Art

Cis-1-aminoindan-2-ol is important as a medical intermediate. For example, this compound is disclosed as a useful intermediate for producing anti-HIV medicines. See J. Med. Chem., 35, 2525 (1992), J. Med. Chem., 35, 1702 (1992), J. Med. Chem., 35, 1685 (1992), etc. Also, as disclosed in J. Chem. Soc. Chem. Commun., 1992, 1673, it is useful as a material for synthesizing optically-active hydroxyesters. Several methods have been disclosed for producing cis-(±)-1-aminoindan-2-ol. For example, Lutz, et al. [J. Am. Chem. Soc., 73, 1639 (1951)] treated trans-(±)-2-bromoindan-1-ol with concentrated aqueous ammonia to form trans-(±)-1-aminoindan-2-ol, amidated it with benzoyl chloride, and then formed a cis-(±)-2-phenyloxazoline derivative by a ring closure, which was thereafter hydrolyzed to obtain the aimed cis-(±)-1-aminoindan-2-ol. Rittle, et al. (Tetrahedron lett., 1987, 521) introduced cis-(±)-1-aminoindan-2-ol to L-phenylalaninamide, separated the resulting mixture by chromatography, and then used a sodium ethoxide treatment to form optically-active cis-1-(−)-aminoindan-2-ol as follows:

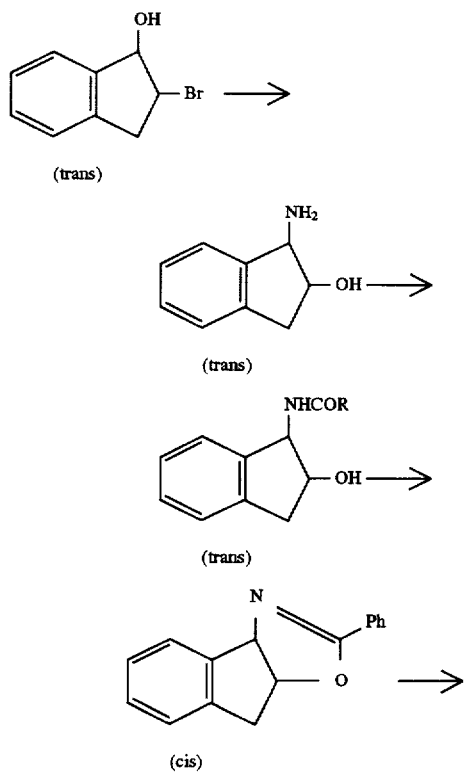

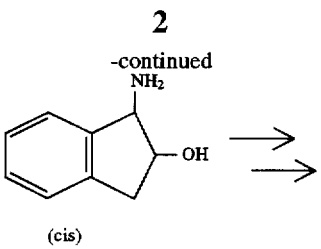

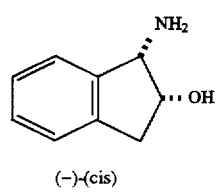

Though the method of Lutz, et al. is relatively effective, it requires multiple steps since the product is made by way of trans-(±)-1-aminoindan-2-ol. Also, it is disadvantageous in that a large quantity of waste water and liquid is yielded as a by-product while the volume efficiency becomes low.

Hassner, et al. [J. Org. Chem., 32, 540 (1967)] heated ethyl-N-(trans-2-iodo-1-indan) carbamate in glyme anhydride to form cis-indano[1,2-d]-2-oxazolidone by a ring closure, which was then hydrolyzed to obtain the aimed cis-(±)-1-aminoindan-2-ol as follows:

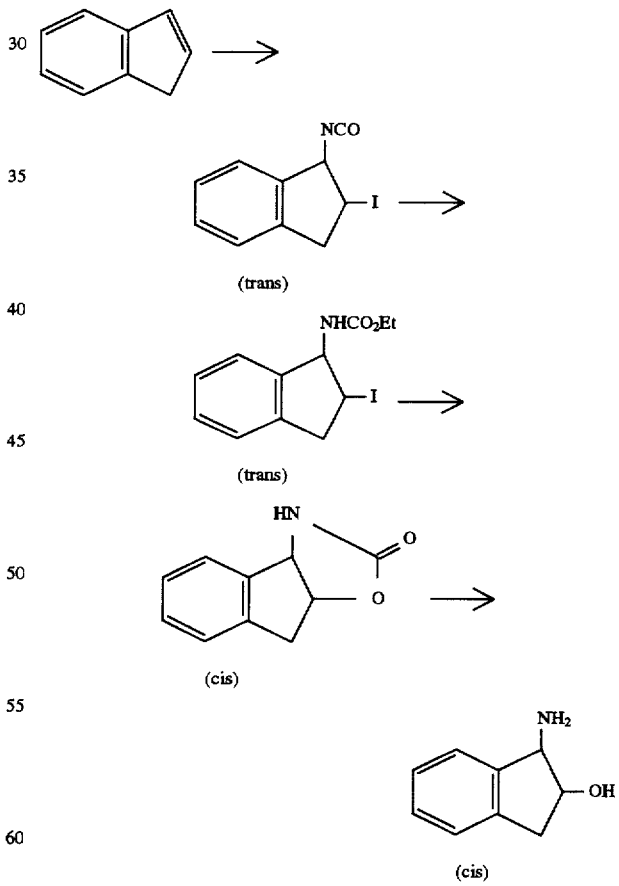

However, though the carbamate used as the starting material here can be obtained by an addition reaction of iodoisocyanate to indene, the method of synthesizing iodoisocyanate is difficult and thus has not been considered industrially applicable. Also, it is disadvantageous in that a high temperature is required for forming the oxazolidone and so on.

Didier, et al. [Tetrahedron, 47, 4941 (1991)] reduced 2-oxoindan-1-methyl carboxylate into optically-active cis-(+)-2-hydroxy-1-methyl carboxylate by using baker's yeast. From this optically-active compound, the aimed cis-(+)-1-aminoindan-2-ol and cis-(−)-1-aminoindan-2-ol were obtained by way of multiple synthesis steps as follows:

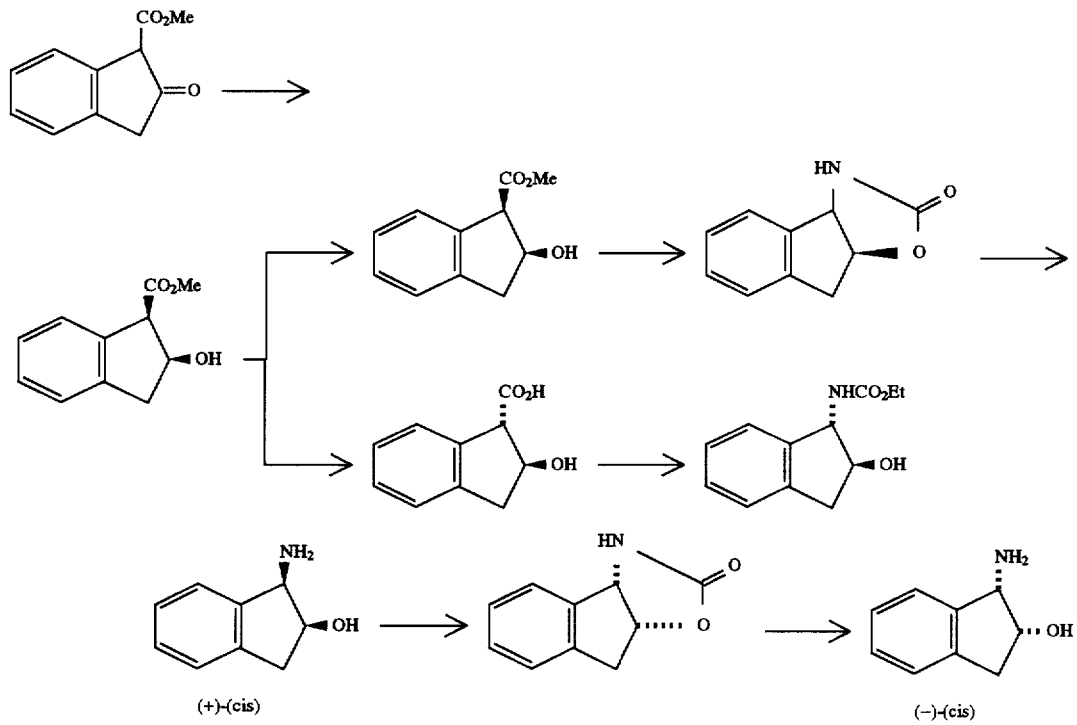

However, this method is disadvantageous in that an unusual reaction agent is necessary and in that yield is low.

As discussed in the foregoing, there has not been known any satisfactory method for producing cis-1-aminoindan-2-ol. Accordingly, this compound has not easily been made at a low cost in an industrial scale.

SUMMARY OF THE INVENTION

The object of the present invention is to provide a method of efficiently producing cis-1-aminoindan-2-ol.

While the above-mentioned method of Lutz, et al. is efficient in that relatively inexpensive materials are used, it is undesirable in that trans-1-aminoindan-2-ol is used as an intermediate. It is nevertheless a remarkable fact that cis-1-aminoindan-2-ol is formed by way of a cis-oxazoline derivative which is formed by a ring closure of a trans-amide derivative. Having thoroughly studied methods for efficiently producing trans-amide and cis-oxazoline derivatives, which are important intermediates, the inventors of the present invention have found it possible to synthesize the trans-amide and cis-oxazoline derivatives by using materials which can be made inexpensively. Thus, the present invention has been accomplished.

Namely, the present invention provides a method of producing a 1,2-di-substituted indan, in which a starting 1,2-di-substituted indan expressed by general formula (I)

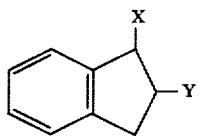

(wherein X is a substituent which can be drawn out under an acidic condition to form a carbocation at 1-position of an indan skeleton, Y is a halogen atom, and X and Y can be in either cis- or trans-configuration forming either a racemic body or an optically active substance) or another starting 1,2-di-substituted indan expressed by general formula (I')

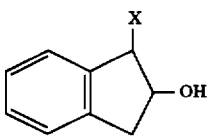

(wherein X is a substituent which can be drawn out under an acidic condition to form a carbocation at 1-position of an indan skeleton, and X and OH group can be in either cis- or trans-configuration forming either a racemic body or an optically-active substance) is reacted, under an acidic condition, with a nitrile expressed by general formula (II)

R—C≡N            (II)

(wherein R is phenyl or a lower alkyl group). When the 1,2-di-substituted indan with a halogen substituent Y expressed by general formula (I) is selected, a trans-amide derivative expressed by general formula (III)

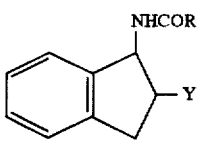

(wherein R is phenyl or a lower alkyl group, Y is a halogen, and NHCOR group and Y are in trans-configuration forming either a racemic body or an optically-active substance) is formed, which is then subjected to a ring closure to generate a cis-oxazoline derivative expressed by general formula (IV)

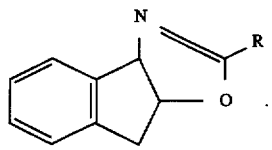

(wherein R is phenyl or a lower alkyl group and oxazoline ring is in cis-configuration forming either a racemic body or an optically-active substance). When the other starting 1,2-di-substituted indan with an OH substituent expressed by general formula (I') is selected, the cis-oxazoline derivative expressed by general formula (IV) is directly produced.

When the cis-oxazoline derivative expressed by general formula (IV) is hydrolyzed, cis-1-aminoindan-2-ol expressed by general formula (V)

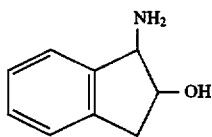

(wherein $NH_2$ and OH groups are in cis-configuration forming either a racemic body or an optically-active substance) is generated.

A reaction in which alcohols react with nitriles to generate amides is well-known as Ritter reaction. For example, synthesis of an amide from a tertiary alcohol was reported by Ritter, et al. [J. Am. Chem. Soc., 70, 4048 (1948)]. This reaction is also applicable to haloalcohols. Lusskin, et al. [J. Am. Chem. Soc., 72, 5577 (1950)] reacted aliphatic halohydrins with nitriles in the presence of concentrated sulfuric acid to synthesize various N-(2-halo-1-ethyl) amides. Further, Wohl [J. Org. Chem., 38, 3099 (1973)] reacted 3-bromo-2-butanol with acetonitriles or benzonitriles in sulfuric acid to obtain 2-amido-3-bromobutanes. It was also reported that these amides were unstable and that they easily formed 2-oxazolines by a ring closure.

However, there has not been known any example of Ritter reaction in which trans-2-haloindan-1-ol is used as haloalcohol. The inventors of the present invention have studied this reaction.

The starting trans-2-haloindan-1-ol includes trans-2-chloroindan-1-ol, trans-2-bromoindan-1-ol, and trans-2-iodoindan-1-ol.

Trans-2-chloroindan-1-ol can be synthesized by the method of Suter, et al. [J. Am. Chem. Soc., 60, 1360 (1938)] in which indene chloride is hydrolyzed. Trans-2-bromoindan-1-ol can be synthesized by the method of Poter, et al. [J. Am. Chem. Soc., 57, 2022 (1935)] using indene and bromine water, the method of Guss, et al. [J. Am. Chem. Soc., 77, 2549 (1955)] in which indene is reacted with N-bromosuccinimide in water, or the like.

When the inventors of the present invention conducted Ritter reaction using trans-2-haloindan-1-ol, the reaction proceeded smoothly to yield the aimed trans-amide derivative expressed by general formula (III). This trans-amide derivative has not been known heretofore. Also, the inventors have found that this amide derivative easily closes a ring, thereby being converted into the cis-oxazoline derivative expressed by general formula (IV). As shown in the above-mentioned report of Wohl and the like, Ritter reaction proceeds with the initial stereospecificity being maintained. Accordingly, the Ritter reaction product of trans-2-haloindan-1-ol is the trans-amide derivative expressed by general formula (III). In accordance with the above-mentioned report of Lutz, et al., the oxazoline derivative formed by a ring closure of the trans-amide derivative expressed by general formula (III) is in cis-configuration. This oxazoline derivative is easily hydrolyzed to form the aimed cis-1-aminoindan-2-ol expressed by general formula (V).

As the result of further studies, the inventors of the present invention have found that, even when the trans-amide derivative expressed by general formula (III) is not isolated, the reaction mixture obtained after the completion of Ritter reaction can be dispersed in water and stirred in this dispersion state to generate the cis-oxazoline derivative expressed by general formula (IV) and the cis-1-aminoindan-2-ol expressed by general formula (V) continuously. Ritter reaction is known to proceed due to the attack of nitrile following the carbocation generation. The generation of trans-amide derivative by the reaction of trans-2-bromo-1-indanol with nitriles under an acidic condition suggests that a carbocation is easily formed at 1-position of the indan skeleton and that the substituent at 1-position can be either in cis- or trans-configuration with respect to the substituent at 2-position.

By choosing the 1,2-di-substituted indan expressed by general formula (I), in which the substituent X at 1-position can easily be drawn out under an acidic condition and the substituent Y at 2-position is a halogen, and studying its reaction with the nitriles expressed by general formula (II), the inventors of the present invention have found that Ritter reaction proceeds to generate the trans-amide derivative expressed by general formula (III).

The substituent X at 1-position of the 1,2-di-substituted indan expressed by general expression (I) includes halogen atoms such as chlorine, bromine, and iodine; and methoxy, ethoxy, phenoxy, methylcarbonyloxy, ethylcarbonyloxy, phenylcarbonyloxy, and hydroxyl groups. More specifically, the compound expressed by general formula (I) includes 2-chloroindan-1-ol, 2-bromoindan-1-ol, 2-iodoindan-1-ol, 1,2-dichloroindan, 1,2-dibromoindan, 1,2-diiodoindan, 1-chloro-2-bromoindan, 1-chloro-2-iodoindan, 2-chloro-1-acetoxyindan, 2-bromo-1-acetoxyindan, 2-iodo-1-acetoxyindan, 2-chloro-1-methoxyindan, 2-bromo-1-methoxyindan, and 2-iodo-1-methoxyindan.

The starting 1,2-dibromoindan can be synthesized by the bromination of indene in accordance with the method of G. E. Heasley, et al. [J. Org. Chem., 45, 5150 (1980)]. According to this literature, the cis/trans ratio obtained by the bromination in acetonitrile is 21/79. Also, 1-chloro-2-bromoindan can be obtained by the reaction of indene with BrCl. Further, in accordance with the method of R. A. Austin, et al. [J. Org. Chem., 34, 1327 (1969)], trans-2-chloro-1-methoxyindan, cis- or trans-1-acetoxy-2-chloroindan, and trans-2-chloro-1-iodoindan can be formed by the reaction of trans-2-chloroindanol with diazomethane, that of 2-chloro-1-indanol with acetyl chloride, and that of indene with ICl, respectively.

The 1,2-di-substituted indan expressed by general formula (I) and the nitrile expressed by general formula (II) are mixed under an acidic condition. In order to attain this acidic condition, fuming sulfuric acid or concentrated sulfuric acid is preferably used. Nevertheless, suitable acidic materials such as perchloric acid, boron trifluoride, methane sulfonate, zeolite, and ion-exchange resins can also be used to attain the desired condition.

The amount of the nitrile expressed by general formula (II) is preferably the same mole as or more than the 1,2-di-substituted indan and can be used in excess. In view of economics and collectibility, acetonitrile is preferably used. Also, the amount of the acid used is preferably the same mole as or more than the 1,2-di-substituted indan expressed by general formula (I). Preferred acids are fuming sulfuric acid and concentrated sulfuric acid. The reaction may not be completed if these acids are used in a less quantity. An inactive solvent may be used for the reaction. The reaction temperature in this process is preferably within the range of −30° C. to 100° C. and more preferably within the range of 10°–100° C. The reaction may proceed too slowly when the temperature is too low, while the yield may be depressed by a side reaction when the temperature is too high. The mixture obtained after the completion of the reaction is turned into the trans-amide derivative expressed by general formula (III) when, for example, dispersed in cold water. When this trans-amide derivative is isolated by an appropriate technique such as filtration or extraction and then processed under a suitable condition, the cis-oxazoline derivative expressed by general formula (IV) is obtained. Since the trans-amide derivative expressed by general formula (III) has a halogen atom as the substituent Y at 2-position, it yields the cis-oxazoline derivative expressed by general formula (IV) when stirred after being dispersed in water. When the cis-oxazoline derivative expressed by general formula (IV) is hydrolyzed, cis-1-aminoindan-2-ol expressed by general formula (V) is obtained. Under an acidic condition, the reaction product, cis-1-aminoindan-2-ol expressed by general formula (V), is in a state of being dissolved in water. Accordingly, after an aqueous solution of this product is washed with a water-insoluble organic solvent such as methylene chloride to remove impurities, an aqueous solution of sodium hydroxide or the like is preferably added thereto. The aimed cis-1-aminoindan-2-ol expressed by general formula (V) precipitates under a strongly alkaline condition. The precipitate can be filtered off and then dried.

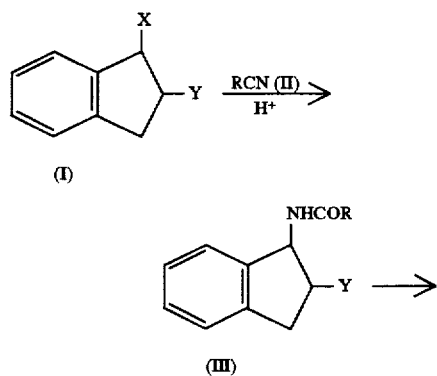

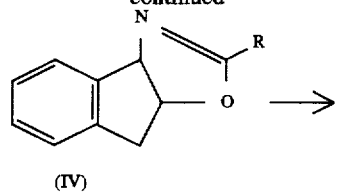

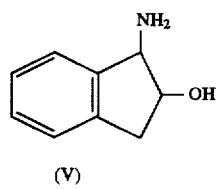

Alternatively, without being isolated, the trans-amide derivative expressed by general formula (III) may be stirred in its dispersion state to yield the aimed cis-1-aminoindan-2-ol expressed by general formula (V). When a water-soluble and highly volatile nitrile such as acetonitrile is used in excess in this case, the nitrile is preferably removed by distillation or the like before the aimed product is washed with a solvent and precipitated. The starting material may be either a racemic body or an optically-active substance. When an optically-active 1,2-di-substituted indan is used as the starting material, the trans-amide derivative expressed by general formula (III), cis-oxazoline derivative expressed by general formula (IV), and final cis-1-aminoindan-2-ol expressed by general formula (V) become optically-active substances.

The optically-active starting trans-2-haloindan-1-ols are obtained in accordance with the method of Boyd, et al. [J. Chem. Soc. Perkin Trans. I, 1982, 2767] in which a racemic trans-2-haloindan-1-ol expressed by general formula (I) is reacted with (−)-menthyloxyacetylchloride to form diastereomer esters of respective halves, which are then separated from each other by chromatography or the like and thereafter treated with diborane. Alternatively, as reported by Kasai, et al. [J. Org. Chem., 49, 675 (1984)], the racemic trans-2-haloindan-1-ol expressed by general formula (I) is acetylated to form a racemic trans-2-halo-1-acetoxyindan, which is then microbiologically hydrolyzed to form these optically-active starting materials. Also, as reported by Imuta, et al. [J. Org. Chem., 43, 4540 (1978)], they can be formed by biological reduction of 2-haloindan-1-on.

For example, cis-(+)-1-aminoindan-2-ol and cis-(−)-1-aminoindan-2-ol are obtained when trans-(−)-2-bromoindan-1-ol and trans-(+)-2-bromoindan-1-ol are used as the starting materials, respectively.

The optically-active starting materials expressed by general formula (I) can be derived from their corresponding optically-active 2-haloindan-1-ols.

Further, the inventors of the present invention have studied Ritter reaction using the above-mentioned 1,2-di-substituted indan expressed by general formula (I'), in which the substituent X at 1-position can easily be drawn out by an acid and the substituent at 2-position is OH, under the above-mentioned reaction condition, and have found that the reaction easily proceeds to generate the cis-oxazoline derivative expressed by general formula (IV). As noted above, this derivative is hydrolyzed to yield the cis-1-aminoindan-2-ol expressed by general formula (V).

The substituent X of the 1,2-di-substituted indan expressed by general formula (I') which can easily be drawn out by an acid to form a carbocation at 1-position includes chlorine, bromine, and iodine atoms as well as hydroxyl, methoxy, ethoxy, phenoxy, methylcarbonyloxy, ethylcarbonyloxy, and phenylcarbonyloxy groups. More specifically, 1,2-indandiol, 1-acetoxy-2-indanol, 1-ethylcarbonyloxy-2-indanol, 1-benzoyloxy-2-indanol, 1-chloro-2-indanol, 1-bromo-2-indanol, 1-iodo-2-indanol, 1-methoxy-2-indanol, 1-ethoxy-2-indanol, or the like can be used as the compound (I').

Trans-1,2-indandiol can be obtained by a reaction of trans-2-bromo-1-indandiol with a dilute aqueous sodium carbonate solution in accordance with the method of A. Gagis, et al [J. Org. Chem., 37, 3181 (1972)]. Cis-1,2-indandiol can be obtained by peroxidation of indene with formic acid in accordance with the method of J. E. Taylor [Synthesis, 1142, (1985)]. Cis-1-methoxy-2-indanol can be obtained by a reaction of cis-1,2-epoxyindan with a copper-pyridine complex in methanol in accordance with the method of M. Imuta, et al [J. Am. Chem. Soc., 101, 3990 (1979)]. As reported by G. H. Posner, et al. [J. Am. Chem. Soc., 99, 8214 (1977)], a mixture of 1-methoxy-2-indanol with a cis/trans ratio of 50/50 can be obtained by a reaction of cis-1,2-epoxyindan with hydrochloric methanol whereas trans-1-methoxy-2-indanol is obtained by a reaction of cis-1,2-epoxyindan with sodium methoxide. The method of G. H. Posner, et al. [J. Am. Chem. Soc., 99, 8208 (1977)] can be used to obtain trans-1-acetoxy-2-indanol by a reaction of cis-1,2-epoxyindan with dilute acetic acid in the presence of neutral alumina.

The starting material may be either a racemic body or an optically-active substance. When an optically-active 1,2-di-substituted indan expressed by general formula (I') is used as the starting material, the cis-oxazoline derivative expressed by general formula (IV) and final cis-1-aminoindan-2-ol expressed by general formula (V) become optically-active substances.

For example, cis-(−)-1-aminoindan-2-ol and cis-(+)-1-aminoindan-2-ol are obtained when trans-(−)-1,2-indandiol and trans-(+)-1,2-indandiol are used as the starting materials, respectively. Also, cis-(−)-1-aminoindan-2-ol and cis-(+)-1-aminoindan-2-ol are obtained when cis-(−)-1,2-indandiol and cis-(+)-1,2-indandiol are used as the starting materials, respectively.

Upon further studies, the inventors of the present invention have also found that, when cis-1,2-epoxyindan expressed by general formula (VI)

(VI)

(wherein epoxy ring is in cis-configuration forming either a racemic body or an optically-active substance) is used as the starting material, Ritter reaction proceeds to yield the aimed cis-1-aminoindan-2-ol expressed by general formula (V). This reaction is supposed to proceed, by way of an addition of nitrile following a cleavage of the cis-epoxide expressed by general formula (VI) with an acid, to form the cis-oxazoline derivative expressed by general formula (IV). When the latter is hydrolyzed, the cis-1-aminoindan-2-ol expressed by general formula (V) is generated. The reaction is illustrated as follows:

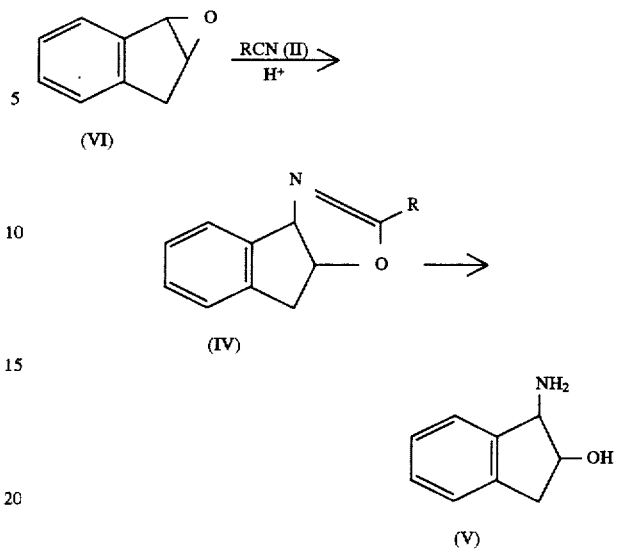

The starting cis-1,2-epoxyindan expressed by general formula (VI) can be obtained by a reaction of trans-2-bromoindan-1-ol with an aqueous sodium hydroxide solution in accordance with Gagis, et al. [J. Org. Chem., 37, 3181 (1972)] or oxidation of indene by a peroxide in accordance with the method of Fringuelli, et al [Org. Prep. Proced. Int., 21, 757 (1989)].

The cis-1,2-epoxyindan expressed by general formula (VI) and the nitrile expressed by general formula (II) is mixed under an acidic condition. Though concentrated sulfuric acid or fuming sulfuric acid is preferably used to obtain this acidic condition, an appropriate acidic material such as perchloric acid, boron trifluoride, methane sulfonate, zeolite, or ion-exchange resins can also be used to attain the desired condition. The amount of nitrile is preferably at least the same mole as the cis-1,2-epoxyindan and may be used in excess as well.

When used for obtaining the acidic condition, concentrated sulfuric acid or fuming sulfuric acid is preferably at least the same mole as the cis-1,2-epoxyindan. The reaction temperature in this process is preferably within the range of −30° C. to 50° C. and more preferably within the range of −30° C. to 0° C. After the reaction is completed, the mixture is dispersed in cold water. The resulting cis-oxazoline derivative expressed by general formula (IV) may be taken out by extraction or the like. Alternatively, without any intermediate processing and extraction, the mixture is dispersed in water and then hydrolyzed to yield the cis-1-aminoindan-2-ol expressed by general formula (V). The reaction temperature of the hydrolysis is preferably between room temperature and 100° C.

When used in excess, nitriles with a high volatility and a high water-solubility, such as acetonitrile, are preferably removed by distillation or the like after the reaction is completed. Impurities can be washed off by a water-insoluble organic solvent such as methylene chloride. Since the aimed cis-1-aminoindan-2-ol is water-soluble under acidic conditions, an aqueous sodium hydroxide solution may be added to the reaction product to attain an alkali condition where the aimed product can be precipitated and subjected to solid-liquid separation.

The starting material may be either a racemic body or an optically-active substance. When an optically-active epoxide is used, the resulting cis-oxazoline derivative expressed by general formula (IV) and cis-1-aminoindan-2-ol expressed by general formula (V) become optically-active substances. For example, cis-(−)-1-aminoindan-2-ol and cis- (+)-1-aminoindan-2-ol are obtained when cis-(+)-1,2-epoxyindan and cis-(−)-1,2-epoxyindan are used, respectively.

The starting cis-(+)-1,2-epoxyindan and cis-(−)-1,2-epoxyindan can be synthesized from (−)-menthylesters of trans-(+)-2-bromoindan-1-ol and trans-(−)-2-bromoindan-1-ol, respectively, in accordance with the above-mentioned method of Boyd, et al.

Reaction mechanisms which are supposed to occur in the foregoing processes of the present invention are schematically illustrated as follows:

As explained in the foregoing, in accordance with the present invention, the 1,2-di-substituted indan or cis-1,2-epoxy indan, which can be prepared at a relatively low cost, is used as a starting material and the trans-amide derivative or cis-oxazoline derivative is formed as an intermediate. As a result, cis-1-aminoindan-2-ol, which has been difficult to produce industrially, can easily be produced with a good efficiency, thereby making it possible to use this product effectively as a medical intermediate.

Process via trans-amide derivative

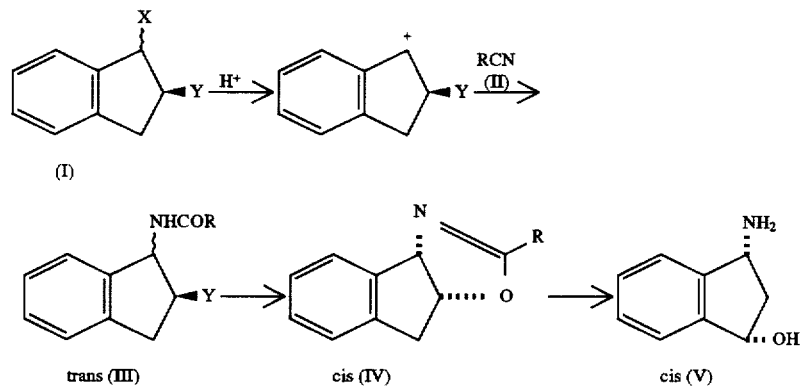

Process without trans-amide derivative

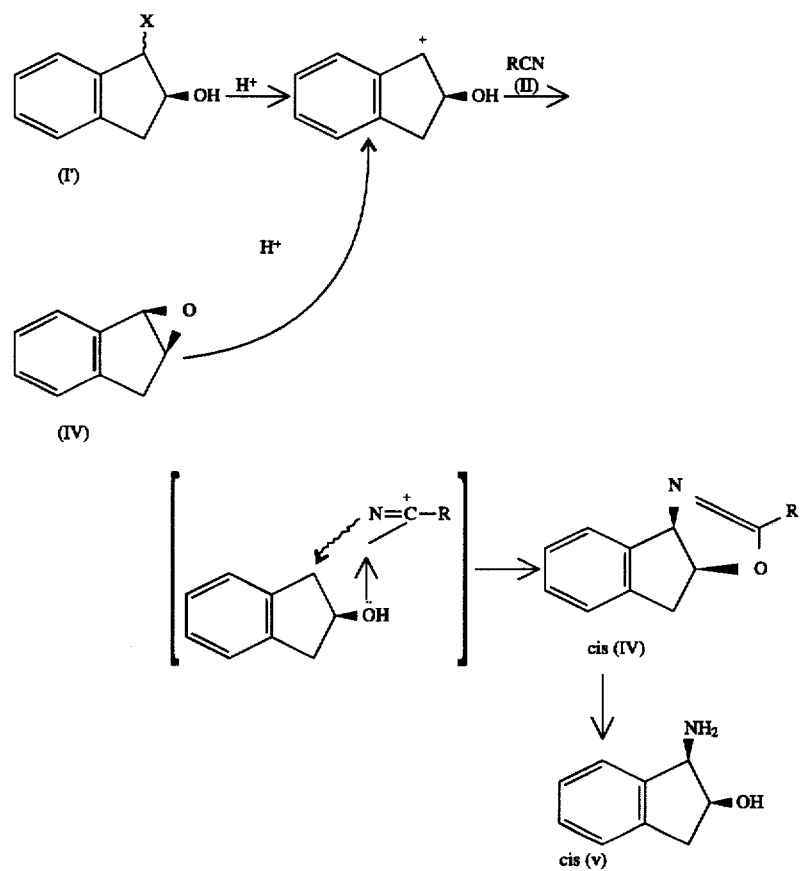

DESCRIPTION OF THE PREFERRED EMBODIMENTS

The present invention will further be explained in detail with reference to the following non-restrictive examples:

EXAMPLE 1

Synthesis of Trans-(±)-amide Derivative (III: Y=Br, R=CH$_3$) from Trans-(±)-2-bromoindan-1-ol (I: X=OH, Y=Br)

Into a 300 ml three-neck flask, 21.3 g (0.1 mol) of trans-(±)-2-bromoindan-1-ol (I) and 150 ml of acetonitrile were introduced. While the resulting mixture was stirred in cool and the temperature was maintained at 10°–15° C. under a suspension condition, 22.5 g of fuming sulfuric acid (containing 25% of SO$_3$) was dropwise added thereto in a period of 1 hour. The slurry was gradually dissolved to form a yellow solution. As the stirring was continued for a while, a white crystal was deposited to yield a slurry. Its thin-layer chromatography showed that the starting material (I) had disappeared. While this slurry was cooled after being stirred at the same temperature for 2 hours, 100 ml of water was added thereto at 15°–20° C.

The white crystal was dissolved and then deposited again. The deposited crystal was filtered off under reduced pressure, washed with water till the wash water becomes neutral, and then dried in vacuo to yield 14.2 g of a white crystal. From the mother liquor and wash water, a secondary crystal was filtered off and processed in the same manner to yield 6.73 g of a white crystal.

A gas chromatography analysis revealed that the purities of the primary and secondary crystals were 96% and 73%, respectively. The IR analysis and $^1$H-NMR analysis of the primary crystal showed that the product was the aimed trans-amide derivative (III: Y=Br, R=CH$_3$). The results of analyses of this product were as follows:

IR (KBr, cm$^{-1}$): 3268 (vNH), 1653 (vC=O) $^1$H-NMR (CDCl$_3$, ppm) δ=7.19–7.74 (4H, m, arom.) 5.55 (1H, dd, CH) 4.33 (1H, q, CH) 3.24 (1H, dd, CH$_2$) 3.54 (1H, dd, CH$_2$) 6.26 (1H, d, NHCO) 2.06 (1H, s, CH$_3$)

EXAMPLE 2

Synthesis of Cis-(±)-1-aminoindan-2-ol (V) from Trans-(±)-amide Derivative (III: Y=Br, R=CH$_3$)

Into a 200 ml three-neck flask, 10.0 g (0.039 mol) of the primary crystal of the trans-(±)-amide derivative (III: Y=Br, R=CH$_3$) and 100 ml of 20% hydrochloric acid were introduced. The mixture was heated while being stirred. As the temperature was raised from 20° C. to 75° C. for a period of about 1 hour, the slurry gradually disappeared to form a colorless transparent solution. This solution was further heated and stirred at 108° C. for 2 hours. Thereafter, when the solution was cooled to room temperature and an aqueous solution of 25% sodium hydroxide was added thereto to attain a pH of 11, a white crystal was obtained. The slurry was filtered under reduced pressure, washed with water, and then dried in vacuo to yield 3.26 g of a white crystal. A gas chromatography analysis revealed that the purity of the product was 99.5%. Since the IR analysis and $^1$H-NMR analysis of the product corresponded to the analyzed values of the above-mentioned Didier, et al., it was confirmed that the product was the aimed cis-(±)-1-aminoindan-2-ol (V). The results of analyses of this product were as follows:

IR (KBr, cm$^{-1}$): 3339 (vNH), 3272 (vNH), 3600 (vOH) $^1$H-NMR (CDCl$_3$, ppm) δ=7.23–7.32 (4H, m, arom.) 4.32 (1H, d, CH) 4.38 (1H, td, CH) 2.94 (1H, dd, CH$_2$) 3.10 (1H, dd, CH$_2$) 2.17 (1H, s, OH) 2.22 (1H, s, NH$_2$)

EXAMPLE 3

Synthesis of Trans-(±)-amide Derivative (III: Y=Br, R=CH$_3$) from Trans-(±)-2-bromoindan-1-ol (I: X=OH, Y=Br)

Into a 200 ml four-neck flask, 50 ml of acetonitrile and 21.3 g (0.1 mol) of trans-(±)-2-bromoindan-1-ol (I) were introduced. While the mixture was stirred, 15.0 g of 97% sulfuric acid was dropwise added thereto at 5°–8° C. in a period of 1 hour. After the mixture was stirred at the same temperature for 1 hour and at 20°–25° C. for 2 hours, a white slurry was formed.

From this reaction mixture, 0.75 g was collected and dispersed in 5 ml of water. The crystal deposited thereby was immediately filtered off and washed with water. Without drying, this crystal was dissolved in 5 ml of chloroform-d. When this solution was subjected to $^1$H-NMR analysis 2 and 4 hours later, it was affirmed that trans-(±)-amide derivative (III: Y=Br, R=CH$_3$) and cis-(±)-oxazoline derivative (IV: R=CH$_3$) had been formed.

The $^1$H-NMR spectrum of thus obtained cis-(±)-oxazoline derivative (IV: R=CH$_3$) was as follows:

$^1$H-NMR (CDCl$_3$, ppm) δ=7.74–7.76 (1H, m, arom.) 7.19–7.74 (3H, m, arom.) 5.99 (1H, td, CH) 5.90 (1H, d, CH) 3.47 (1H, d, CH$_2$) 3.64 (1H, dd, CH$_2$) 2.43 (3H, s, CH$_3$)

From the integrated ratio of methyl protons in (III) and (IV), the compositions at two and four hours were calculated as follows:

|      | (III)      | (IV)       |
|------|------------|------------|
| 2 hr | 54.7 mol % | 36.0 mol % |
| 4 hr | 17.3 mol % | 65.3 mol % |

In view of these results, it was affirmed that trans-(±)-amide derivative (III: Y=Br, R=CH$_3$) was unstable and gradually closed a ring to form cis-(±)-oxazoline derivative (IV: R=CH$_3$).

The whole slurry obtained after the completion of the reaction was left for 24 hours and then, while being cooled, introduced into 215 g of an aqueous solution of 10% sodium hydrogencarbonate. The crystal deposited thereby was filtered off, washed with 100 ml of water, and dried in vacuo to yield 23.8 g (raw yield: 93.7%) of crude trans-(±)-amide derivative (III: Y=Br, R=CH$_3$) as a white crystal.

EXAMPLE 4

Synthesis of Cis-(±)-1-aminoindan-2-ol (V) from Trans-(±)-2-bromoindan-1-ol (I: X=OH, Y=Br)

Into a 200 ml four-neck flask, 50 ml of acetic acid, 21.3 g (0.1 mol) of trans-(±)-2-bromoindan-1-ol (I), and 4.52 g (0.11 mol) of acetonitrile were introduced. While the mixture was stirred, 12.1 g (0.12 mol) of 97% sulfuric acid was dropwise added thereto at 23°–25° C. in a period of 35 minutes. The crystal totally disappeared. The reaction liquid was further stirred at room temperature for 20 hours. When dispersed into 200 ml of water, the reaction liquid became a white slurry. As this slurry was heated at 60° C. for 6 hours while being stirred, the crystal was totally dissolved. The reaction liquid was cooled to room temperature, washed twice with 100 ml of methylene chloride, and then subjected to liquid separation. When an aqueous solution of 25% sodium hydroxide was added to the water phase to attain a pH of 11, a white crystal was deposited. This crystal was filtered off under reduced pressure, washed with 100 ml of water, and then dried in vacuo to yield 5.33 g of cis-(±)-1-aminoindan-2-ol (I) as a white crystal. Its purity determined by a liquid chromatography was 96.9%.

EXAMPLE 5

Synthesis of Cis-(±)-1-aminoindan-2-ol (V) from Trans-(±)-2-bromoindan-1-ol (I: X=OH, Y=Br)

Into a 200 ml four-neck flask, 21.3 g (0.1 mol) of trans-(±)-2-bromoindan-1-ol (I) and 50 ml of acetonitrile were introduced. At 25° C., 15.2 g of 97% sulfuric acid was dropwise added to the mixture in a period of about 1 hour. The reaction liquid was further stirred at room temperature for 2 hours. The slurry-like reaction mixture was dispersed in 140 ml of water and stirred at 60° C. for 5 hours. After the excess acetonitrile was distilled off under reduced pressure, the mixture was further stirred at 60° C. for 1 hour and then cooled to room temperature. After impurities were extracted by methylene chloride, an aqueous solution of 25% sodium hydroxide was added to the remaining mixture to attain a pH of 11. The crystal deposited thereby was filtered off under reduced pressure, washed with 80 ml of water, and then dried in vacuo to yield 10.35 g of cis-(±)-1-aminoindan-2-ol (I) as a white crystal. The results of its analyses were as follows:

Melting point: 127.4°–129.2° C.

Purity determined by liquid chromatography: 98.2%

Purity determined by perchloric acid titration: 99.4%

EXAMPLE 6

Synthesis of Cis-(±)-1-aminoindan-2-ol (V) from Cis-(±)-1,2-epoxyindan (VI)

Into a 200 ml four-neck flask, 9.24 g (70 mmol) of cis-(±)-1,2-epoxyindan (IV) and 35 ml of acetonitrile were introduced. While the mixture was stirred in cool, 10.62 g of 97% sulfuric acid was dropwise added thereto at 20°–25° C. in a period of 30 minutes. The reaction mixture was further stirred at room temperature for 1 hour. Then, acetonitrile was distilled off under reduced pressure. The remaining mixture was further stirred at 60° C. for 1 hour and then cooled to room temperature. Impurities were extracted off from the mixture with 20 ml and 10 ml of methylene chloride. An aqueous solution of 25% sodium hydroxide was added to the water phase to attain a pH of 11. The crystal deposited thereby was filtered off and then dried in vacuo to yield 4.76 g (raw yield: 45.7%) of cis-(±)-1-aminoindan-2-ol (V) as a grayish white crystal. From thus obtained crystal, 2 g was taken out and washed with 6 ml of acetonitrile at 10° C. The washed crystal was filtered off and then dried in vacuo to yield 1.68 g of the aimed product (V) as a white crystal. Its purity determined by a liquid chromatography was 98.9%.

EXAMPLE 7

Synthesis of Cis-(±)-1-aminoindan-2-ol (V) from Mixture of Trans- and Cis-(±)-1,2-dibromoindans (I: X=Y=Br)

1) Synthesis of (±)-1,2-dibromoindan from indene

Into a 1000 ml four-neck flask, 78.1 g (purity: 96%; 0.646 mol) and 75 ml of acetonitrile were introduced and cooled in an ice bath. To this mixture, a solution in which 103.2 g (0.646 mol) of bromine had been dissolved in 75 ml of acetonitrile was added dropwise at 0°–5° C. in a period of 6 hours. The resulting mixture was stirred at the same temperature for 1.5 hours to finally yield a yellow acetonitrile solution of 1,2-dibromoindan (purity determined by HPLC: 87.3%).

2) Synthesis of cis-(±)-1-aminoindan-2-ol (V) from (±)-1,2-dibromoindan

Into a 1000 ml four-neck flask, 259.5 g of an acetonitrile solution of 1,2-dibromoindan (corresponding to bromination of 0.559 mol of indene) was introduced. It was then heated to 40° C. To this solution, 86.57 g (0.839 mol) of 97% sulfuric acid was dropwise added at 40°–46° C. in a period of 1.5 hours. The resulting mixture was stirred at the same temperature for 5 hours. According to an HPLC analysis, about 15% of 1,2-dibromoindan was remaining in the mixture. To this mixture, 43.29 g of sulfuric acid was further added. The resulting mixture was stirred at 50°–60° C. for 1.5 hours. According to an HPLC analysis, 1,2-dibromoindan had almost disappeared yielding 11.0% of trans-amide derivative (III: R=CH$_3$) and 25.3% of cis-oxazoline derivative (IV: R=CH$_3$).

When 840 ml of water was added to this mixture, a brown crystal deposited. This crystal was gradually dissolved to form an ocher solution when heated at 60° C. while being stirred. When this solution was further stirred for 4.5 hours, the cis-oxazoline peak disappeared from the HPLC.

Under normal pressure, the solution was subjected to azeotropic distillation with 150 ml of acetonitrile at 96°–97° C. After the resulting mixture was cooled to 25° C., dichloromethane was added thereto. This mixture was stirred and then subjected to liquid separation. The water phase was collected in a 2000 ml beaker and 25% sodium hydroxide was added thereto to attain a pH of 9–10. The deposited crystal was filtered off under reduced pressure, washed with water, and then dried to yield 48.3 g (yield from indene: 57.8%) of cis-1-aminoindan-2-ol as a white crystal.

EXAMPLE 8

Synthesis of Cis-(±)-1-aminoindan-2-ol (V) from Cis-(±)-1,2-epoxyindan (VI)

Into a 300 ml four-neck flask, 10.0 g (75.8 mmol) of cis-(±)-1,2-epoxyindan (VI), 50 ml of acetonitrile, and 40 ml of dichloromethane were introduced. This mixture was cooled to −30° C. in a dry ice/acetone bath. To this mixture, 11.14 g (113.6 mmol) of 100% sulfuric acid (prepared from 97% sulfuric acid and fuming sulfuric acid) was dropwise added at −30° to −27° C. in a period of 1 hour. When left for 1 hour to return to room temperature, the mixture became white and turbid to form a slurry. An HPLC analysis of the contents revealed that 46.8% of cis-oxazoline derivative (IV: R=CH$_3$) had been generated. No cis-amide derivative (III: R=CH$_3$) was detected. As the mixture was heated while 72 ml of water being added thereto, 100 ml of an azeotrope of acetonitrile/dichloromethane/water was distilled off in a period of 1 hour. The remaining mixture was cooled to room temperature, washed twice with 100 ml of dichloromethane, and then subjected to liquid separation. The water phase was adjusted to a strongly alkali state by an addition of 25% sodium hydroxide. The crystal deposited thereby was filtered off under reduced pressure, washed with water, and then dried to yield 7.53 g (yield: 66.8%) of cis-(±)-1-aminoindan-2-ol (V) as a white crystal. Its purity determined by an HPLC was 95.5%.

EXAMPLE 9

Synthesis of Cis-(±)-1-aminoindan-2-ol (V) from Cis-(±)-1,2-epoxyindan (VI)

Into a 300 ml four-neck flask, 10.0 g (75.8 mmol) of cis-(±)-1,2-epoxyindan (VI) and 40 ml of acetonitrile were introduced. This mixture was cooled to −16° C. in an ice/salt bath. To this mixture, 10.62 g (113.6 mmol) of fuming sulfuric acid (containing 25% of sulfuric anhydride) was dropwise added at −13° to −17° C. in a period of 1.5 hour. The mixture was left for 1.5 hour to return to room temperature. An HPLC analysis of the contents revealed that 21.2% of cis-oxazoline derivative (IV: R=CH$_3$) had been generated while no trans-amide derivative (III': R=CH$_3$, Y=OH) was detected. Then, 72 ml of water was added thereto. The resulting mixture was treated in the same manner as Example 8 to yield 5.62 g (yield: 49.8%) of cis-(±)-1-aminoindan-2-ol (V) as a white crystal. Its purity determined by an HPLC was 98.7%.

EXAMPLE 10

Synthesis of Cis-(±)-1-aminoindan-2-ol (V) from Trans-(±)-1,2-indandiol (II: X=OH)

Into a 100 ml four-neck flask, 4.48 g (30.3 mmol) of trans-(±)-1,2-indandiol (II) and 40 ml of acetonitrile were introduced. This mixture was suspended. While this suspension was stirred at room temperature, 6.14 g (60.6 mmol) of 97% sulfuric acid was added thereto at room temperature in a period of 20 minutes. The temperature within the mixture increased from 19° C. to 35° C. The slurry was completely dissolved to form a slightly yellow transparent solution. The solution was stirred at 24° C. for 1 hour and then at 60° C. for 1 hour. An HPLC analysis of the contents revealed that 70.8% of cis-oxazoline derivative (IV: R=CH$_3$) had been generated, while no trans-amide derivative (III': R=CH$_3$, Y=OH) was detected. Then, 30 ml of water was added thereto and the resulting mixture was stirred at 60° C. for 3 hours. Acetonitrile was removed by azeotropic distillation. The remaining mixture was washed with dichloromethane and then subjected to liquid separation. When an aqueous solution of 25% sodium hydroxide was added to the water phase, a crystal deposited. This crystal was filtered off under reduced pressure, washed with water, and then dried to yield 2.70 g (yield: 59.7%) of cis-(±)-1-aminoindan-2-ol (V) as a white crystal. Its purity determined by an HPLC was 97.7%.

EXAMPLE 11

Synthesis of Cis-(±)-1-aminoindan-2-ol (V) from Trans- and Cis-(±)-1,2-indandiol (I': X=OH)

Into a 100 ml four-neck flask, 2.0 g (13.33 mmol) of (±)-1,2-indandiol (I': cis/trans=81.1/15.7) and 30 ml of acetonitrile were introduced. This mixture was suspended. While this suspension was stirred at 30° C., 2.02 g (20.0 mmol) of 97% sulfuric acid was dropwise added thereto in a period of 30 minutes. As sulfuric acid was added, the slurry of diol decreased. After the resulting mixture was stirred at 60° C. for 2 hours, an HPLC revealed that diol disappeared while 48.8% of cis-oxazoline derivative (IV: R=CH$_3$) was formed. Then, 25 ml of water was added thereto and the mixture was stirred at 60° C. for 24 hours. The reaction liquid became a red brown solution. Acetonitrile was distilled off under reduced pressure. The remaining mixture was washed three times with dichloromethane. By an addition of 25% sodium hydroxide, the water phase was adjusted to a strongly alkali state. This water phase was extracted twice with 100 ml of dichloromethane and the resulting dichloromethane phase was concentrated under reduced pressure to yield 1.10 g of a grayish white crystal. Its HPLC analysis revealed that the it contained 89.2% of cis-(±)-1-aminoindan-2-ol (V) and 9.3% of cis-(±)-2-hydroxy-1-acetoaminoindan which was a hydrolysis intermediate formed when the compound (V) was generated from the cis-oxazoline derivative (IV: R=CH$_3$).

EXAMPLE 12

Synthesis of Cis-(±)-1-aminoindan-2-ol (V) from (±)-1-Methoxyindan-2-ol (I': X=OCH$_3$)

1) Synthesis of (±)-1-methoxyindan-2-ol (II: X=OCH$_3$) from cis-(±)-1,2-epoxyindan (VI)

Into a 500 ml four-neck flask, 120 ml of methanol was introduced and 16.4 g (0.304 mol) of sodium methoxide powder was dissolved therein. At 30° C., 20.0 g (0.152 mol) of cis-(±)-1,2-epoxyindan (VI) dissolved in 80 ml of methanol was dropwise added thereto in a period of 90 minutes. After this mixture was stirred at 30° C. for 5 hours, 100 ml of water was added thereto. The resulting mixture was neutralized with 270 ml of 1N hydrochloric acid and then methanol was distilled off under reduced pressure. The remaining mixture was extracted twice with 200 ml of dichloromethane. The extracted phase was dried for one night with sodium sulfuric anhydride. The dichloromethane phase was concentrated under pressure to yield 28.5 g of an orange oily substance. When it was purified by a silica gel column chromatography in which chloroform was used as a developing solvent, 16.32 g (yield: 65.5%) of trans-(±)-1-methoxyindan-2-ol (I') was obtained as a pale yellow oil. Its purity determined by an HPLC analysis was 95.4%.

The $^1$H-NMR spectrum and IR spectrum of this product corresponded to those of G. H. Posner, et al [J. Am. Chem. Soc., 99, 8214 (1977)].

2) Synthesis of cis-(±)-1-aminoindan-2-ol (V) from trans-(±)-1-methoxyindan-2-ol (I': X=OCH$_3$)

Into a 300 ml three-neck flask, 70 ml of acetonitrile and 10.0 g (0.061 mol) of trans-(±)-1-methoxyindan-2-ol (I') were introduced. At 30° C., 11.7 g (0.122 mol) of methane sulfonic acid dissolved in 35 ml of acetonitrile was dropwise added thereto in a period of 1 hour. After this mixture was stirred at 60° C. for 4 hours, an HPLC analysis revealed that 60.0% of cis-oxazoline derivative (IV: R=CH$_3$) had been generated therein. Then, 50 ml of water was added thereto and the mixture was stirred at 60° C. for 3 hours. Acetonitrile was distilled off under reduced pressure. The remaining mixture was washed twice with 100 ml of dichloromethane. By an addition of an aqueous solution of sodium hydroxide, the pH of the water phase was adjusted to 10. The crystal deposited thereby was filtered off under reduced pressure, washed with water, and then dried to yield 3.36 g of a white crystal. According to an HPLC analysis, this crystal contained 79.5% of cis-(±)-1-aminoindan-2-ol (V). Also, it contained 18.6% of cis-(±)-1-acetoamidoindan-2-ol which was a by-product formed when the hydrolysis was insufficient. This by-product was separated by a silica gel column chromatography in which chloroform was used as a developing solvent. Its structure was affirmed since its IR spectrum corresponded to that of an authentic sample [synthesized from cis-(±)-1-aminoindan-2-ol and acetyl chloride].

EXAMPLE 13

Synthesis of Cis-(±)-1-aminoindan-2-ol (V) from Trans-(±)-1-methoxyindan-2-ol (II: X=OCH$_3$)

In 100 ml of acetonitrile, 14.5 g of trans-(±)-1-methoxyindan-2-ol (I') was dissolved. This mixture was heated to 30° C. To this mixture, 11.49 g (113.6 mmol) of 97% sulfuric acid dissolved in 50 ml of acetonitrile was dropwise added at the same temperature in a period of 1 hour. Then, the mixture was stirred at 60° C. for 3 hours. An HPLC analysis revealed that 53.3% of cis-oxazoline derivative (IV: R=CH$_3$) had been formed. To this mixture, 72 ml of water was added. The resulting mixture was stirred at 60° C. for 4 hours and then treated in the same manner as Example 12 to yield 4.34 g of a white crystal. According to an HPLC analysis, this crystal contained 53.4% of cis-(±)-1-aminoindan-2-ol (V) and 46.6% of cis-(±)-1-acetoamidoindan-2-ol.

EXAMPLE 14

Synthesis of Cis-(±)-oxazoline Derivative (IV: R= CH$_3$) from Cis-(±)-1,2-epoxyindan (VI: R=CH$_3$)

Into a 300 ml four-neck flask, 10.0 g (75.75 mmol) of cis-(±)-1,2-epoxyindan (VI), 170 ml of acetonitrile, and 170 ml of dichloromethane were introduced. This mixture was cooled to −16° C. while being stirred. At the same temperature, 14.2 g (151.5 mmol) of fuming sulfuric acid was dropwise added thereto in a period of 1 hour. Then, in a period of 1 hour, the temperature of the mixture was raised to 23° C., where the mixture was further stirred for 4 hours. The crystal deposited thereby was filtered off, washed with 20 ml of acetonitrile and with 50 ml of dichloromethane, and then dried under reduced pressure to yield 9.98 g of a sulfate of crude cis-(±)-oxazoline derivative (IV: R=CH$_3$) as a white crystal. Into a 50 ml eggplant-type flask, 10 ml of water was introduced and 1.0 g (25 mmol) of sodium hydroxide was dissolved therein. To this mixture, 20 ml of dichloromethane and then 3.0 g of the sulfate obtained above were added. After being stirred for 10 minutes, the mixture was subjected to a liquid separation. The water phase was further extracted with 20 ml of dichloromethane. The dichloromethane phases were combined together and dried with sodium sulfuric anhydride. When the solvent was distilled off, 1.22 g of cis-(±)-oxazoline derivative (IV: R=CH$_3$) was obtained as a white crystal. Its melting point was 65.0°–66.5° C. The $^1$H-NMR spectrum corresponded to that of the cis-(±)-oxazoline derivative (IV: R=CH$_3$) in Example 3.

EXAMPLE 15

Synthesis of Optically-active Cis-(−)-1-aminoindan-2-ol (V) from Optically-active Trans-(−)-1,2-indandiol (I': X=OH)

In 40 ml of acetonitrile, 3.0 g (20.1 mmol) of trans-(−)-1,2-indandiol (I': trans-configuration: 98.0%; cis-configuration: 2.0%; optical purity: 100% e.e.) was dissolved. At room temperature, 3.2 g (31.7 mol) of 97% sulfuric acid was dropwise added thereto in a period of 30 minutes. After the resulting mixture was stirred at room temperature for 1 hour, the compound (I') disappeared from an HPLC. To the reaction liquid, 20 ml of water was added. Immediately thereafter, the mixture was heated and 42 ml of an acetonitrile/water azeotrope was distilled off under normal pressure. Then, the mixture was subjected to a reflux for 1.5 hours to complete the reaction. The reaction liquid was cooled to room temperature and washed twice with 10 ml of dichloromethane. Then, its pH was adjusted to 10.5 by an addition of an aqueous solution of 25% sodium hydroxide. The grayish white scaly crystal deposited thereby was filtered off under reduced pressure, washed with a small quantity of water, and then dried under reduced pressure to yield 1.77 g of cis-(−)-1-aminoindan-2-ol (V) as a primary crystal. Then, the mother liquid after the deposition of the crystal was extracted with dichloromethane and the extracted phase was concentrated to yield 0.69 g of the compound (V) as a secondary crystal.

Results of analysis of primary crystal
Purity: 97.5% (HPLC internal standard material method)
Pure contents: 1.73 g (yield: 57.7%)
Optical purity: 99.8% e.e.
Results of analysis of secondary crystal
Purity: 91.6% (HPLC internal standard material method)
Pure contents: 0.63 g (yield: 21.0%)
Optical purity: 99.8% e.e.

EXAMPLE 16

Synthesis of Optically-active Cis-(−)-1-aminoindan-2-ol (V) from Optically-active Cis-(−)-1,2-indandiol (I': X=OH)

Into a 100 ml four-neck flask, 3.0 g (20.1 mmol) of cis-(−)-1,2-indandiol (I': cis-configuration: 97.5%; trans-configuration: 2.5%; optical purity: 100% e.e.) were introduced and dissolved therein. At room temperature, 3.2 g (31.7 mmol) of 97% sulfuric acid was dropwise added thereto in a period of 30 minutes. After the resulting mixture was stirred at room temperature for 1 hour, the compound (I') disappeared from an HPLC. To the reaction liquid, 20 ml of water was added. Immediately thereafter, the mixture was heated and 42 ml of an acetonitrile/water azeotrope was distilled off under normal pressure. Under a reflux, the mixture was stirred for 1.5 hours to complete the reaction. The reaction liquid was cooled to room temperature and washed twice with 10 ml of dichloromethane. Then, its pH was adjusted to 10.5 by an addition of an aqueous solution of 25% sodium hydroxide. The grayish white scaly crystal deposited thereby was filtered off under reduced pressure, washed with a small quantity of water, and then dried in vacuo to yield 0.78 g of cis-(−)-1-aminoindan-2-ol (V) as a primary crystal. Then, the mother liquid was extracted with dichloromethane and the extracted phase was concentrated to yield 1.93 g of the compound (V) as a secondary crystal.

Results of analysis of primary crystal
Purity: 98.9% (HPLC internal standard material method)
Pure contents: 0.77 g (yield: 25.7%)
Optical purity: 99.9% e.e.
Results of analysis of secondary crystal
Purity: 98.7% (HPLC internal standard material method)
Pure contents: 1.90 g (yield: 63.3%)
Optical purity: 99.9% e.e.

EXAMPLE 17

Synthesis of Optically-active Cis-(−)-1-aminoindan-2-ol (V) from Optically-active Cis-(+)-1,2-epoxyindan (VI)

Into a 300 ml flask, 30 ml of acetonitrile was introduced. It was then cooled to −16° C. At this temperature, a solution in which 10.0 g (75.8 mmol) of cis-(+)-1,2-epoxyindan (VI: optical purity: 95.1% e.e.) had been dissolved in 10 ml of acetonitrile as well as 11.5 g (113.6 mmol) of 97% sulfuric acid were dropwise added thereto independently at the same time in a period of 2 hours 10 minutes. The cooling was stopped so that the reaction liquid gradually returned to room temperature. When 72 ml of water was added thereto, a white crystal deposited. The reaction mixture was heated and 74 ml of a water/acetonitrile azeotrope was distilled off. The remaining mixture was stirred for 1 hour under a reflux. The white crystal of the oxazoline derivative disappeared to form a transparent solution. This reaction liquid was cooled to room temperature and washed twice with 50 ml of dichloromethane. The pH of the water phase was adjusted to 10.5 by an addition of an aqueous solution of 25% sodium hydroxide. The grayish white scaly crystal deposited thereby was filtered off under reduced pressure, washed with a small quantity of water, and then dried in vacuo to yield 6.69 g (yield: 59.3%) of cis-(−)-1-aminoindan-2-ol (V). The chemical purity and optical purity of this crystal were 96.9% and 99.6% e.e., respectively.

EXAMPLE 18

Synthesis of Optically-active Cis-(+)-1-aminoindan-2-ol (V) from Optically-active Cis-(−)-1,2-epoxyindan (VI)

Into a 300 ml flask, 30 ml of acetonitrile was introduced. It was then cooled to −18° C. At this temperature, a solution in which 10.0 g (75.8 mmol) of cis-(−)-1,2-epoxyindan (VI: optical purity: 94.0% e.e.) had been dissolved in 10 ml of acetonitrile as well as 11.5 g (113.6 mmol) of 97% sulfuric acid were dropwise added thereto independently at the same time in a period of 2 hours 30 minutes. Then, the reaction liquid was returned to room temperature. When 72 ml of water was added to the reaction liquid, a white crystal deposited. The reaction mixture was heated while being stirred. Under normal pressure, 75 ml of a water/acetonitrile azeotrope was distilled off. The remaining mixture was stirred for 1 hour under a reflux. The white crystal of the oxazoline derivative disappeared to form a transparent solution. This reaction liquid was cooled to room temperature and washed twice with 50 ml of dichloromethane. The pH of the water phase was adjusted to 10.5 by an addition of an aqueous solution of 25% sodium hydroxide. The grayish white scaly crystal deposited thereby was filtered off under reduced pressure, washed with a small quantity of water, and then dried in vacuo to yield 6.78 g (yield: 60.0%) of cis-(+)-1-aminoindan-2-ol (V). The chemical purity and optical purity of this crystal were 98.2% and 98.2% e.e., respectively.

EXAMPLE 19

Synthesis of Cis-(±)-1-aminoindan-2-ol (V) from Trans-(±)-2-chloroindan-1-ol (I: X=OH; Y=Cl)

Into a 300 ml flask, 23.6 g (140 mmol) of trans-(±)-2-chloroindan-1-ol (I: X=OH, Y=Cl) and 70 ml of acetonitrile were introduced. While this mixture was stirred, 23.8 g (238 mmol) of 98% sulfuric acid was dropwise added thereto at 20°–30° C. in a period of 100 minutes. To this mixture, 190 ml of water was added. The resulting mixture was stirred at 60° C. for 2 hours. Under normal pressure, 130 ml of an acetonitrile/water azeotrope was distilled off therefrom. To the remaining mixture, 50 ml of water was added. The mixture was further subjected to a reflux for 3 hours and then cooled to room temperature. After insoluble matters were filtered off under reduced pressure, the filtrate was washed with 60 ml of dichloromethane. The pH of the water phase was adjusted to 11 by an addition of an aqueous solution of 25% sodium hydroxide. The deposited crystal was filtered off under reduced pressure, washed with a small quantity of water, and then dried in vacuo to yield 9.76 g of a white crystal. According to an analysis based on the internal standard material method, the crystal contained 6.95 g (yield: 33.2%) of the aimed product (V). The mother liquid of the above-mentioned filtration was extracted with 200 ml of dichloromethane. The resulting organic phase was concentrated to yield 2.25 g of a white crystal. According to an analysis based on the internal standard material method, this crystal contained 1.42 g (yield: 6.8%) of the aimed product (V).

EXAMPLE 20

Synthesis of Optically-active Cis-(+)-1-aminoindan-2-ol (V) from Optically-active Trans-(+)-1,2-indandiol (I': X=OH)

Into a 100 ml reaction flask, 3.0 g (20.1 mmol) of trans-(+)-1,2-indandiol (I': trans-configuration: 98.3%; cis-configuration: 1.7%; optical purity: 93.0% e.e.) and 40 ml of acetonitrile were introduced. While this mixture was stirred at room temperature, 4.06 g (40.2 mmol) of 97% sulfuric acid was added thereto in a period of 30 minutes. The resulting mixture was stirred at the same temperature for 1 hour and then at 60° C. for 4 hours. After 20 ml of water was added thereto, the mixture was further stirred at room temperature for one night. Under normal pressure, 44 ml of an acetonitrile/water azeotrope was distilled off. The remaining mixture was further subjected to a reflux for 3.5 hours. This reaction liquid was cooled to room temperature and then washed twice with 10 ml of dichloromethane. The pH of the water phase was adjusted to 11 by an addition of an aqueous solution of 25% sodium hydroxide. The crystal deposited thereby was dissolved in dichloromethane. After an extraction, the organic phase was concentrated to yield 2.37 g of the product (V) as a white crystal. According to an analysis based on the internal standard material method, the purity of the crystal was 96.7%. The yield of the aimed product was 2.29 g (yield: 76.3%). Its optical purity was 96.8% e.e.

EXAMPLE 21

Synthesis of Optically-active Cis-(+)-1-aminoindan-2-ol (V) from Optically-active Cis-(+)-1,2-indandiol (I': X=OH)

Into a 100 ml reaction flask, 3.0 g (20.1 mmol) of cis-(+)-1,2-indandiol (I': cis-configuration: 97.2%; trans-configuration: 2.8%; optical purity: 93.0% e.e.) and 40 ml of acetonitrile were introduced. While this mixture was stirred at room temperature, 4.06 g (40.2 mmol) of 97% sulfuric acid was added thereto in a period of 30 minutes. The resulting mixture was stirred at the same temperature for 1 hour and then at 60° C. for 4 hours. After 20 ml of water was added thereto, the mixture was heated. Until the temperature within the mixture became 101° C., an acetonitrile/water azeotrope was distilled off under normal pressure. The remaining mixture was further stirred for 2 hours under a reflux and then cooled to room temperature. This reaction liquid was washed twice with 10 ml of dichloromethane. The pH of the water phase was adjusted to about 11 by an addition of an aqueous solution of 25% sodium hydroxide. After being extracted with dichloromethane, the extracted phase was washed with 10 ml of saturated brine. The dichloromethane solution was concentrated under reduced pressure to yield 2.37 g of the product (V) as a white crystal. According to an HPLC analysis based on the internal standard material method, the purity of the crystal was 96.5%. The yield of the aimed product was 2.29 g (yield: 76.3%). Its optical purity was 97.6% e.e.

EXAMPLE 22

Synthesis of Optically-active Cis-(−)-1-aminoindan-2-ol (V) from Optically-active Trans-(+)-2-bromo-1-indanol (I: X=OH, Y=Br)

Into a 10 ml eggplant-type flask, 1.07 g (5.0 mmol) of trans-(+)-2-bromo-1-indanol (I: X=OH, Y=Br; optical purity: 81.6% e.e.) and 2.6 ml of acetonitrile were introduced. While this mixture was stirred with a magnetic stirrer and cooled in a water bath, 0.76 g (7.5 mmol) of 97% sulfuric acid was dropwise added thereto in a period of 2 hours. The resulting mixture was stirred at room temperature for 1 hour and then 6.5 ml of water was added thereto. After an acetonitrile/water azeotrope was distilled off under a reduced pressure of 200 mmHg at a bath temperature of 40° C., the remaining mixture was heated to 80° C. under normal pressure and then stirred at the same temperature for 4.5 hours. This reaction liquid was cooled to room temperature and then washed twice with 10 ml of dichloromethane. After a liquid separation, the pH of the water phase was adjusted to 11 by an addition of an aqueous solution of 25% sodium hydroxide. This phase was extracted with 10 ml of dichloromethane three times and then dried with sodium sulfate anhydride. After the solvent was distilled off from the remaining liquid, 0.60 g of a crude product was obtained. This product was dissolved in 97% sulfuric acid and then washed twice with 10 ml of dichloromethane. Thereafter, while this solution was cooled to room temperature, 25% sodium hydroxide was added thereto to attain a pH of 7. Then, the solution was washed twice with 10 ml of dichloromethane. By an addition of 25% sodium hydroxide, the pH of the solution was adjusted to 11. Thereafter, this solution was extracted with dichloromethane, dried with sodium sulfate anhydride, and then evaporated to dryness in vacuo to yield 0.38 g of cis-(−)-1-aminoindan-2-ol (V) as a white crystal (yield: 51.0%). According to an HPLC, its chemical purity and optical purity were 98.5% and 82.0% e.e., respectively.

EXAMPLE 23

Synthesis of Optically-active Cis-(+)-1-aminoindan-2-ol (V) from Optically-active Trans-(−)-2-bromo-1-indanol (I: X=OH, Y=Br)

Into a 10 ml eggplant-type flask, 1.07 g (5.0 mmol) of trans-(−)-2-bromo-1-indanol (I: X=OH, Y=Br; optical purity based on specific rotation: 42.5%) and 2.6 ml of acetonitrile were introduced. While this mixture was stirred with a magnetic stirrer, 0.76 g (7.5 mmol) of 97% sulfuric acid was dropwise added thereto in a period of 2 hours at room temperature. The resulting mixture was stirred at room temperature for 1 hour and then 6.5 ml of water was added thereto. After an acetonitrile/water azeotrope was distilled off under a reduced pressure of 200 mmHg at 40° C., the remaining mixture was stirred for 4.5 hours at 60° C. This reaction liquid was cooled to room temperature and then washed twice with 10 ml of dichloromethane. An aqueous solution of 25% sodium hydroxide was added to the water phase to attain a pH of 7. The resulting solution was washed twice with 10 ml of dichloromethane. Then, the pH of the water phase was adjusted to 11 by an addition of an aqueous solution of 25% sodium hydroxide. This phase was extracted with 10 ml of dichloromethane three times. The extracted phase was dried with sodium sulfate anhydride and then evaporated to dryness in vacuo to yield 0.47 g of cis-(+)-1-aminoindan-2-ol (V) as a white crystal (yield: 63.0%). According to an HPLC, its chemical purity and optical purity based on specific rotation were 98.8% and 42.0%, respectively.

What is claimed is:

1. A method of producing a cis-oxazoline derivative expressed by formula (IV)

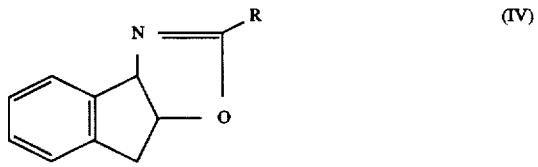

wherein R is phenyl or a lower alkyl group and oxazoline ring is in cis-configuration forming either a racemic body or an optically-active substance; said method comprising the step of subjecting a trans-amide derivative expressed by formula (III)

wherein R is phenyl or a lower alkyl group, Y is a halogen, and NHCOR group and Y are in trans-configuration forming either a racemic body or an optically-active substance to a ring closure under neutral to acidic conditions in a semi-polar solvent.

2. A method of producing a cis-oxazoline derivative as defined in claim 1 in which a trans-amide derivative wherein R is methyl group in formula (III) is used.

* * * * *